(12) United States Patent
Noda et al.

(10) Patent No.: US 6,418,777 B1
(45) Date of Patent: Jul. 16, 2002

(54) GAS SENSOR

(75) Inventors: Keiichi Noda, Ichinomiya; Kazuo Taguchi, Nagoya; Hisaharu Nishio, Tokai; Katsuhisa Yabuta, Komaki, all of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 09/219,824

(22) Filed: Dec. 23, 1998

(30) Foreign Application Priority Data

Dec. 26, 1997 (JP) .............................. 9-367546
Dec. 17, 1998 (JP) ........................... 10-358341

(51) Int. Cl.⁷ ......................... G01N 19/10; G01N 27/26
(52) U.S. Cl. ......................................... 73/23.2; 204/424
(58) Field of Search ............................ 73/23.2, 23.31, 73/31.05; 204/424, 426, 428; 60/274

(56) References Cited

U.S. PATENT DOCUMENTS

| | | | |
|---|---|---|---|
| 3,920,172 A | | 11/1975 | Rhee |
| 4,040,930 A | | 8/1977 | Dillon |
| 5,039,972 A | * | 8/1991 | Kato et al. ..................... 338/34 |
| 5,329,806 A | * | 7/1994 | McClanahan et al. ..... 73/31.05 |
| 5,688,390 A | * | 11/1997 | Yamauchi et al. .......... 204/426 |
| 5,739,414 A | * | 4/1998 | Paulus et al. ............... 73/23.31 |
| 5,817,920 A | * | 10/1998 | Kuisell et al. .............. 73/23.31 |
| 6,063,249 A | * | 5/2000 | Duce et al. .................. 204/424 |

FOREIGN PATENT DOCUMENTS

| | | |
|---|---|---|
| EP | 0 704 697 A1 | 4/1996 |
| JP | 60-211345 | 10/1985 |
| JP | 02-001540 | 1/1990 |
| JP | 6-23964 | 6/1994 |
| JP | 9-257745 A | 10/1997 |
| JP | 10-253578 A | 9/1998 |

OTHER PUBLICATIONS

Translation of portions of Japanese Utility Model No. 6–23964.

\* cited by examiner

*Primary Examiner*—Hezron Williams
*Assistant Examiner*—Jay L Politzer
(74) *Attorney, Agent, or Firm*—Brinks Hofer Gilson & Lione

(57) ABSTRACT

A gas sensor 1 includes an outer cylinder 18, a metallic shell 3, and a sensor element 2. The metallic shell 3 is disposed inside the outer cylinder 18. The sensor element 2 is disposed in a through-hole 30 formed in the metallic shell 3 and is adapted to detect a component of a gas to be measured. A sealing material layer 32 is mainly made of glass and is disposed between the outer surface of the sensor element 2 and the inner surface of the metallic shell 3 or between the outer surface of the sensor element 2 and the inner surface of an insulator 4 disposed between the metallic shell 3 and the sensor element 2. Cushion layer 33 and 34 are each made of a porous inorganic substance. At least either the cushion layer 33 or 34 is disposed so as to abut one end of the sealing material layer 32. A gas sensor according to the present invention includes a sensor element featuring lower susceptibility to mechanical shock or thermal stress induced by different rates of contraction between a sealing material layer and an adjacent component element, as well as excellent durability.

9 Claims, 7 Drawing Sheets

(a) Stress Concentration (b) Stress Dispersion (a)

(b)

(a)

(b)

GAS SENSOR

BACKGROUND OF THE INVENTION

1. Field of the Invention

The present invention relates to a gas sensor for detecting a component of a gas to be measured (hereinafter referred to as a measurement gas), such as an oxygen sensor, an HC sensor, an $NO_x$ sensor, or a like sensor.

2. Description of the Related Art

Conventionally, there has been known a gas sensor composed of an outer cylinder, a metallic shell disposed inside the outer cylinder, and a sensor element disposed inside the metallic shell for detecting a component of a measurement gas. In a gas sensor having such a structure, a gap between the outer surface of the sensor element and the inner surface of the metallic shell or that between the outer surface of the sensor element and the inner surface of an insulator disposed between the metallic shell and the sensor element is generally filled with a sealing material layer, as of glass.

For example, an oxygen sensor for automobile use is often mounted in an exhaust manifold or an exhaust pipe located near a suspension system and tires. In this case, a stone flipped from a tire may hit the sensor so that a mechanical shock acts on the sensor, or the sensor may be subjected to a strong thermal shock caused by splashing of water during exposure to high temperature. Further, the sensor element of the sensor has a coefficient of thermal expansion smaller than that of the sealing material layer. Therefore, in a glass sealing step, the sensor element receives a radial compressive force due to a thermal history (heating/cooling), so that stress concentration occurs in a boundary region between a portion of the sensor element covered with the sealing material layer and an uncovered portion. If a mechanical shock caused by a flipped stone or the like or a thermal shock caused by splashing of water acts on the sensor in such a state, a resultant stress acts at a boundary region (hereinafter referred to as "sealing boundary portion") between the portion of the sensor element covered with the sealing material layer and the uncovered portion, so that the sensor element is easily broken.

SUMMARY OF THE INVENTION

An object of the present invention is to provide a gas sensor in which stress caused by application of a mechanical or thermal shock on the sensor does not concentrate at the sealing boundary portion and which therefore has excellent durability.

To achieve the above object, a gas sensor of the present invention comprises an outer cylinder, a metallic shell, a sensor element, a sealing material layer, and a cushion layer. The metallic shell is joined to the outer cylinder. The sensor element is disposed inside the metallic shell and is adapted to detect a component of a measurement gas. The sealing material layer is mainly made of glass and is disposed between the outer surface of the sensor element and the inner surface of the metallic shell or between the outer surface of the sensor element and the inner surface of an insulator disposed between the metallic shell and the sensor element. The cushion layer is made of a porous inorganic substance and is disposed on at least one side of the sealing material layer with respect to the axial direction of the sensor element.

The above-described structure of the gas sensor of the present invention prevents local application of a strong bending stress onto the sealing boundary portion, which would otherwise occur when mechanical or thermal shock acts on the sensor element.

DESCRIPTION OF THE PREFERRED EMBODIMENTS

Figure 1:
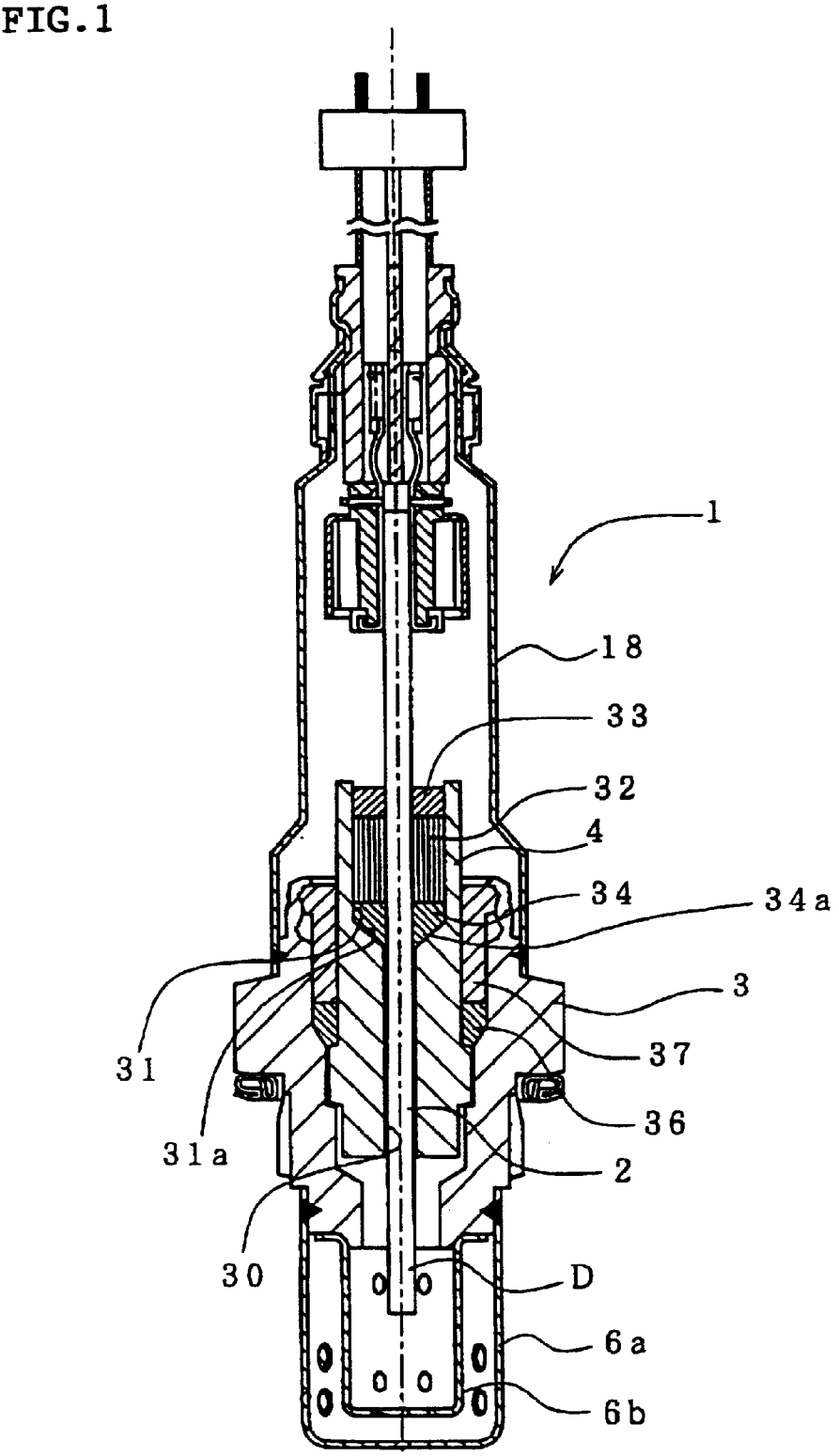
FIG. 1 is a longitudinal, sectional view of a gas sensor of an embodiment of the present invention.

When cushion layers are disposed at opposite ends of the sealing material layer 32 as shown in FIG. 1, it becomes possible to alleviate stress concentration which would otherwise occur in the sensor element 2 at opposite ends of the sealing material layer 32, thereby further improving the durability of the sensor element 2. In this case, the cushion layers 33 and 34 may be of different materials or of the same material.

As shown in FIG. 1, the sensor element 2 has an elongated shape with a sensing portion D formed at a tip end thereof and is inserted through the metallic shell 3 such that the sensing portion D projects therefrom. In this case, the cushion layer 34 which is in contact with the end of the sealing material layer 32 located closer to the tip of the sensor element 2 contains filler particles which are superior in heat resistance to glass contained in the sealing material layer 32, as well as binder particles which partially fill gaps among filler particles, are superior in heat resistance to glass contained in the sealing material layer, and are lower in softening temperature than the filler particles.

Specifically, the cushion layer 34 is more susceptible to high temperature than is the sealing material layer 32. Therefore, in the cushion layer 34, the filler particles, which are superior in heat resistance to glass contained in the sealing material layer 32, are bonded by the binder particles, which are lower in softening temperature than the filler particles but are superior in heat resistance to glass contained in the sealing material layer. Accordingly, sufficient heat resistance is attained. In this case, the filler particles may be formed mainly of $Al_2O_3$ or talc, and are preferably formed mainly of $Al_2O_3$ in view of its excellent heat resistance. The binder particles are preferably of clay, for example, since clay particles can fuse together at a temperature of forming the sealing material layer 32 (a sealing temperature).

The cushion layer 34 is provided for the purpose of uniformly pressing the outer surface of the sensor element 2 to thereby prevent stress concentration in the sensor element at the sealing boundary portion. However, the employment of the cushion layer 34 causes a problem when the cushion layer 34 is formed by a process in which the sensor element 2 is inserted into a cavity 31 formed in the metallic shell 3 or the insulator 4, a material power for forming the cushion layer 34 (or powder compact) is placed in the cavity 31 and pressed, and the material powder is then heated to a predetermined sealing temperature. That is, when the cushion layer 34 is formed in the above-described manner, the filling density of the cushion layer 34 is increased through application of a downward pressing force. However, the pressing force is not transmitted uniformly to the outer surface of the sensor element 2, because pressure is not uniformly transmitted within powder, unlike the case of fluid. In order to solve this problem, the configuration in which the sensor element 2 is inserted through the metallic shell 3 such that the sensing portion D projects therefrom and that the cushion layer 34 is disposed in contact with the end of the sealing material layer 32 located closer to the sensing portion D is improved as shown in FIG. 1. Specifically, the cavity 31 is formed such that the diameter at the front-end side with respect to the axial direction of the sensor element 2 (hereinafter simply referred to as the front-end side) is smaller than that at the rear-end side with respect to the axial direction of the sensor element 2 (hereinafter simply referred to as the rear-end side). By virtue of this structure, the filling density of the material powder at a smaller diameter portion of the cavity 31 can be increased when the material powder is filled into the cavity 31, and a pressure is applied to the 10 upper portion of the powder layer. Therefore, the pressing force that the cushion layer 34 applies to the outer surface of the sensor element 2 can be made uniform to a considerable degree.

Figure 6:
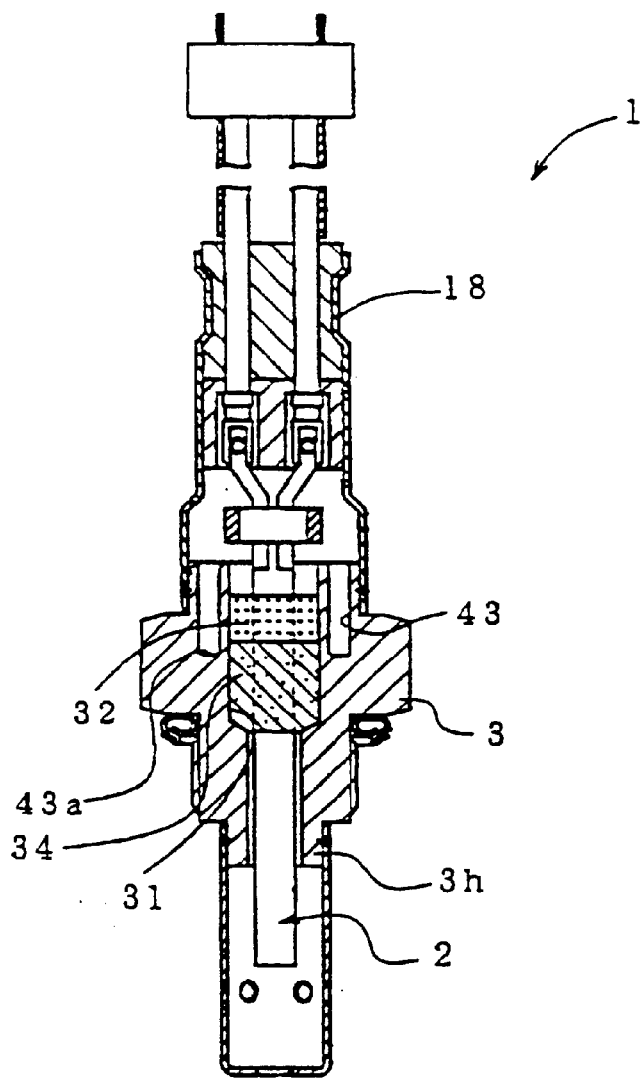
FIG. 6 is a longitudinal, sectional view showing a modification of the gas sensor of FIG. 1.
Figure 6:
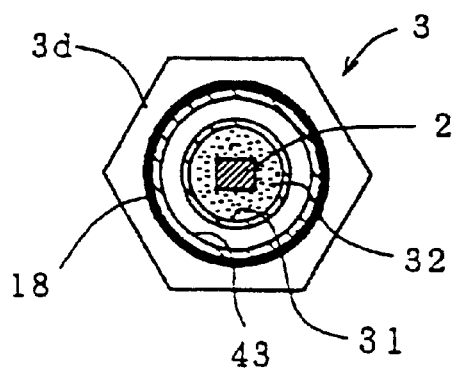

The above gas sensor 1 of the present invention may assume the following configuration. Specifically, as shown in FIG. 6, an annular groove 43 that surrounds the sealing material layer 32 is formed in the metallic shell 3 by cutting out a portion of the metallic shell 3. The annular groove 43 is located between the inner surface of the outer cylinder and the surface of the cavity 31 of the metallic shell 3, through which the sensor element 2 is passed.

In the above-configuration, when the sensor 1 is in a heated state and water is splashed thereon, thus causing an abrupt temperature variation, the annular groove 43 serves as a heat-insulating layer. Also, when the sensor is subjected to a mechanical impulsive force caused by impinging foreign matter such as a pebble, a portion of the outer cylinder or a portion of the metallic shell which serves as an outer wall portion defining the annular groove 43 acts as a cushion for absorbing the mechanical impulsive force. Therefore, the annular groove 43 mitigates the thermal or mechanical shock acting on the sealing material layer 32, so that the effect of the present invention can be enhanced.

FIG. 1 shows an embodiment of a gas sensor of the present invention. An oxygen sensor 1 is adapted to detect the concentration of oxygen contained in an exhaust gas emitted from an automobile or a like apparatus. The oxygen sensor 1 includes an elongated ceramic element 2 (sensor element). The tip of the ceramic element 2 is exposed to high-temperature exhaust gas flowing through an exhaust pipe.

Figure 2:
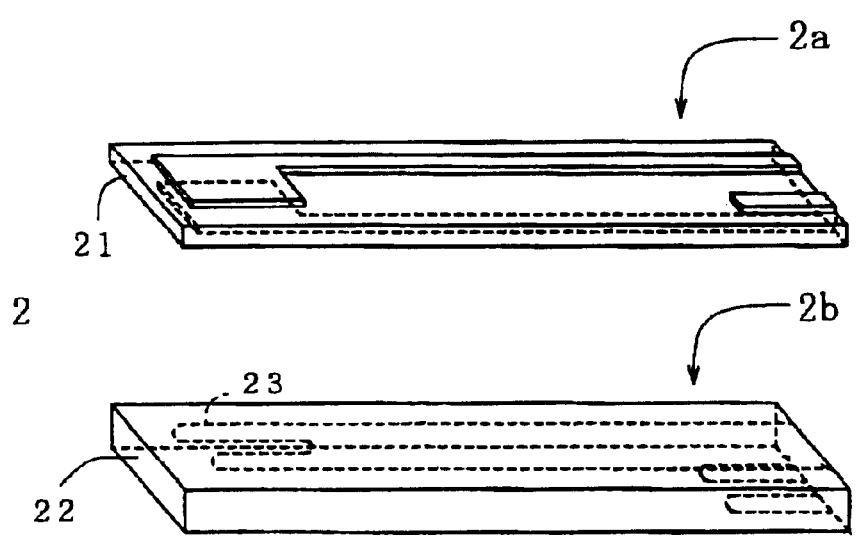
FIG. 2 is an explanatory view showing the structure of a ceramic element serving as a sensor element of the gas sensor of FIG. 1.

The ceramic element 2 is an elongated sheet having a rectangular section. As shown in FIG. 2, the ceramic element 2 is a laminate of an oxygen concentration cell element 2a and a heater 2b. The oxygen concentration cell element 2a has an elongated sheet form. The heater 2b also has an elongated sheet form and is adapted to heat the oxygen concentration cell element 2a to a predetermined activation temperature. The oxygen concentration cell element 2a is made of an oxygen-ion conductive solid electrolyte 21. A typical example of such a solid electrolyte 21 is $ZrO_2$ obtained through solid solution of $Y_2O_3$ or CaO. Alternatively, a solid solution of $ZrO_2$ and an oxide of an alkali earth metal or rare earth metal may be used. The heater 2b is a known ceramic heater composed of a ceramic substrate 22 and a resistance heating pattern 23. The resistance-heating pattern 23 is made of a high-melting-point metal and is embedded in the ceramic substrate 22.

As shown in FIG. 1, the ceramic element 2 having the above structure is inserted through a through-hole 30 of an insulator 4 disposed inside the metallic shell 3 and is fixed to the insulator 4. A cavity 31 is formed in the insulator 4 such that one end of the cavity 31 communicates with the rear end of the through-hole 30, and the other end of the cavity 31 opens at the rear end surface of the insulator 4. The cavity 31 has a diameter larger than that of the through-hole 30. A space which is defined by the outer surface of the ceramic element 2 and the inner surface of the insulator 4 which defines the cavity 31 is filled for sealing purpose with a sealing material layer 32. The sealing material layer 32 is mainly made of glass (for example, crystallized zinc silica boric-acid glass; softening temperature 684° C.).

Within the cavity 31, cushion layers 33 and 34 are formed on opposite sides of the sealing material layer 32. The cushion layers 33 and 34 are made of a porous inorganic substance. The porous inorganic substance for the cushion layer 34 includes filler particles and binder particles. The filler particles are superior in heat resistance to glass contained in the sealing material layer 32. The binder particles partially fill gaps among the filler particles and have a softening temperature lower than that of the filler particles. For example, the filler particles are oxide particles formed mainly of $Al_2O_3$, and the binder particles are clay particles.

The clay particles may be mainly composed of hydrous alumino-silicate. For example, the clay particles may be mainly composed two or more clay minerals (or their composite substances) selected from the group consisting of allophane, imogolite, hisingerite, smectites, kaolinite, halloysite, montmorillonite, illite, vermiculite, and dolomite. From the point of view of oxide components, the clay particles may contain $SiO_2$ and $Al_2O_3$ and, as needed, may further contain singly or in combination $Fe_2O_3$, $TiO_2$, CaO, MgO, and K20. For example, in the present embodiment, the clay particles contain 84% by weight $Al_2O_3$ and 10% by weight $SiO_2$ as oxides and kaolinite and dolomite in appropriate amounts.

The tip end of the cavity 31 of the insulator 4 tapers down in order to form a reduced diameter portion 31a. Similarly, the tip end of the cushion layer 34 also tapers down according to the reduced diameter portion 31a, thereby forming a reduced diameter portion 34a.

The cushion layer 33 is formed of talc particles and crystallized glass having a softening temperature slightly lower than that of glass contained in the sealing material layer 32 (e.g., crystallized zinc silica boric-acid glass; softening temperature 680° C.).

The above-mentioned sealed structure of the ceramic element 2 and the insulator 4 is manufactured in the following manner, for example. First, a material powder compact for forming the cushion layer 34 is manufactured. In the present embodiment, $Al_2O_3$ powder serving as the filler particles and clay powder serving as the binder particles are mixed. The resulting mixture is pressed into a powder compact 50 shown in FIG. 4(a). The powder compact 50 has a through-hole 50b formed in a central portion thereof and in the axial direction thereof. The circumferential surface of the tip end of the powder compact 50 tapers down to form a tapered surface 50a corresponding to the reduced diameter portion 31a of the cavity 31 of the insulator 4.

Figure 4:
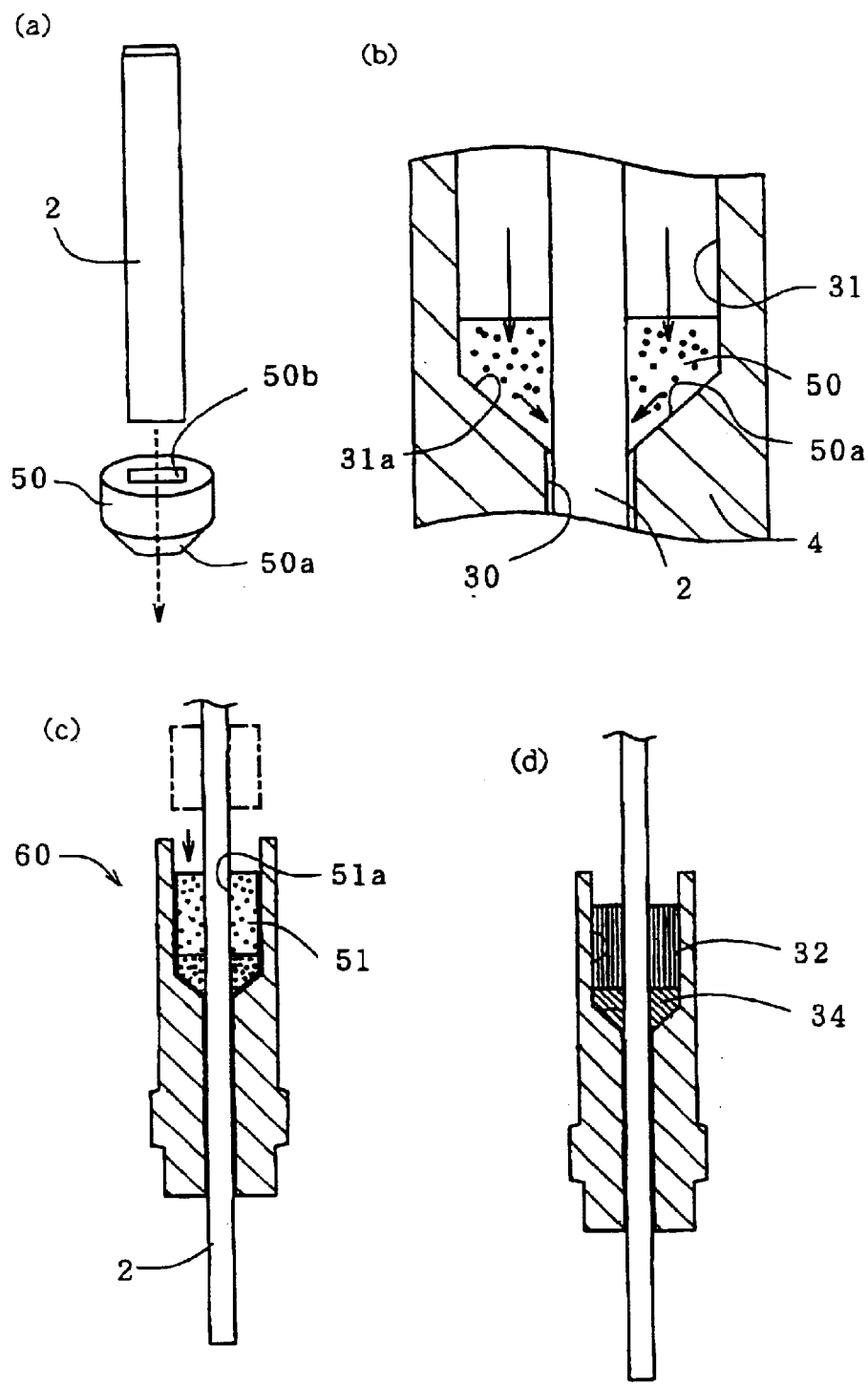
FIG. 4 is an explanatory view illustrating a process for manufacturing the gas sensor of FIG. 1.

Next, the ceramic element 2 is inserted through the through-hole 50b formed in the powder compact 50. Then, the ceramic element 2 is inserted from its tip through the through-hole 30 formed in the insulator 4. The powder compact 50 is placed in the cavity 31 formed in the insulator 4 and is lightly pressed against the insulator 4 in the axial direction of the ceramic element 2. In this case, as shown in FIG. 4(b), the tapered surface 50a of the powder compact 50 is pressed against and in close contact with the reduced diameter portion 31a of the cavity 31. Accordingly, the tapered portion of the powder compact 50 is subjected to a radial reaction effected by the reduced diameter portion 31a and presses the outer surface of the ceramic element 2. Next, as shown in FIG. 4(c), an inorganic material powder which is mainly composed of glass is formed into a cylindrical shape, yielding a powder compact 51. The powder compact 51 is fitted onto the ceramic element 2 from the rear end of the ceramic element 2 in such a manner that the ceramic element 2 is inserted through a through-hole 51a formed in the powder compact 51. Thus, the powder compact 51 is placed in the cavity 31 adjacent to the powder compact 50, thereby obtaining an insulator-sensor-element assembly 60.

The insulator-sensor-element assembly 60 is heated to 850° C. As a result, the powder compact 51 becomes the sealing material layer 32 through fusion of the inorganic material powder which is mainly composed of glass, thereby sealing the ceramic element 2 against the insulator 4. The powder compact 50 becomes the cushion layer 34 as shown in FIG. 4(d) through fusion of the clay powder while $Al_2O_3$ particles are dispersed.

Figure 5:
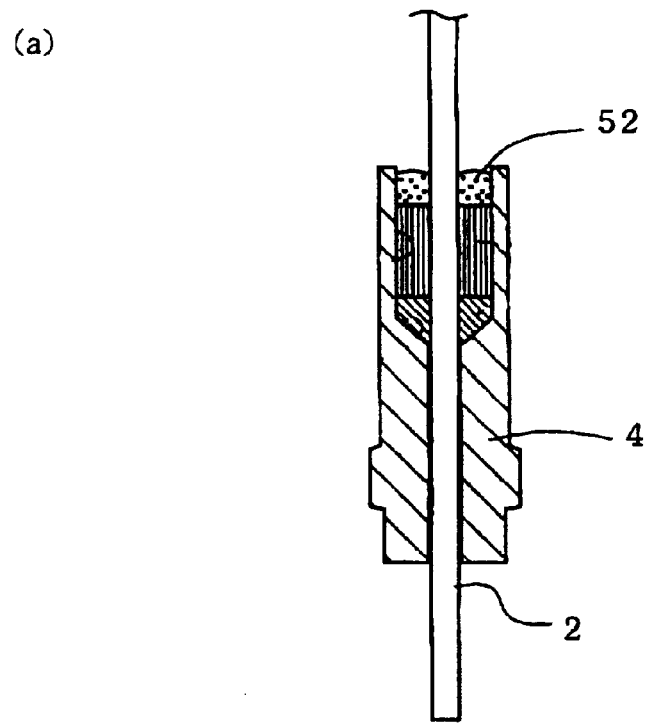
FIG. 5 is an explanatory view continued from FIG. 4.
Figure 5:
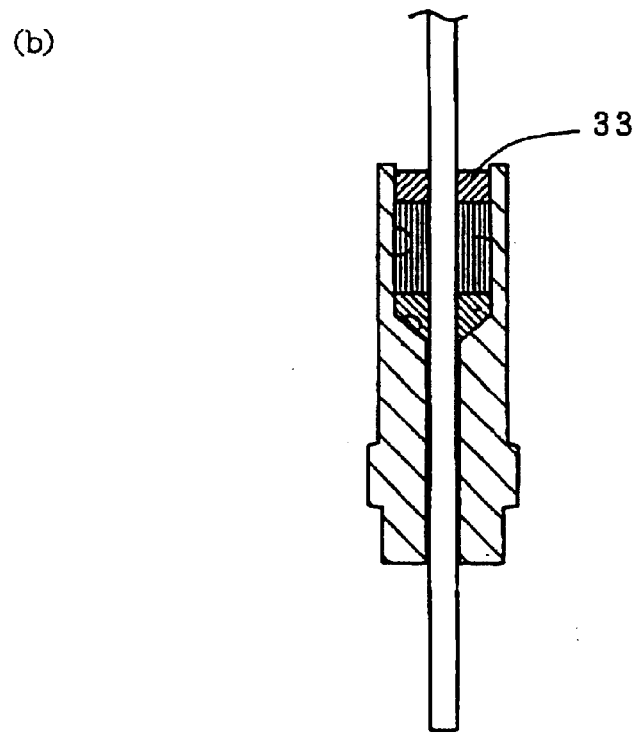

Next, as shown in FIG. 5(a), a material powder 52 (in the present embodiment, a mixed powder of talc and crystallized zinc silica boric-acid glass) for the cushion layer 33 is filled into a space between the ceramic element 2 and the insulator 4 at a rear portion of the cavity 31. The charged material powder 52 is lightly pressed. Subsequently, the insulator-sensor-element assembly 60 is again heated to 800° C. As a result, as shown in FIG. 5(b), the charged material powder 52 becomes the cushion layer 33 through fusion of the crystallized glass powder. In place of directly filling the material powder 52 into the cavity 31, the material powder 52 may be pressed into a compact, which is then placed in the cavity 31.

Next, as shown in FIG. 1, a talc ring 36 and a caulking ring 37 are fitted between the insulator 4 and the metallic shell 3. The rear-end portion of the metallic shell 3 is caulked toward the insulator 4 via the caulking ring 37 to thereby fix the insulator 4 and the metallic shell 3. Double protection covers 6a and 6b of metal are fixedly attached to the tip portion of the metallic shell 3 through laser welding or resistance welding (for example, spot welding) in such a manner as to cover a projected portion of the ceramic element 2. A rear end portion of the metallic shell 3 is fitted into a tip end portion of the outer cylinder 18. At the fitted overlap of the metallic shell 3 and the outer cylinder 18, the metallic shell 3 and the outer cylinder 18 are circumferentially welded together (for example, through laser welding). At the fitted overlap, the metallic shell 3 and the outer cylinder 18 may be connected through circumferential caulking in place of laser welding.

Figure 3:
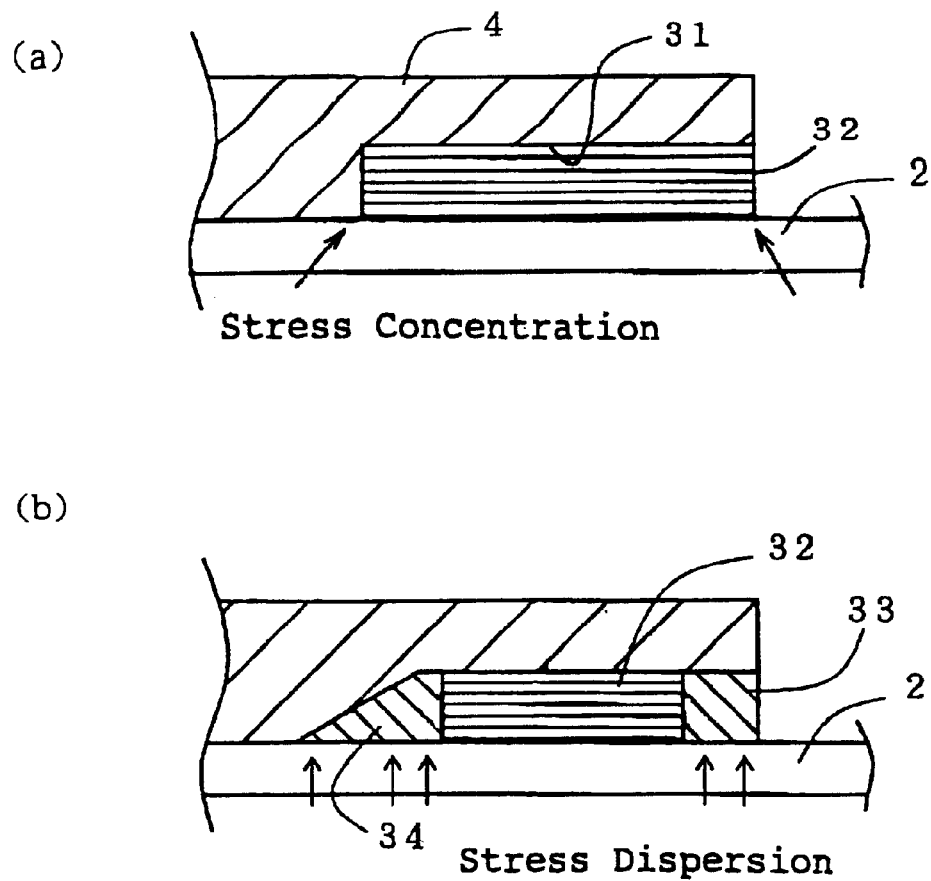
FIG. 3 is an explanatory view showing the action of a cushion layer.

The oxygen sensor 1 is often attached to an exhaust manifold or an exhaust pipe located near a suspension system and tires of a vehicle. In this case, a flipped stone or the like may hit the sensor, or the sensor may be subjected to a strong thermal shock caused by splashing of water during exposure to high temperature. According to the configuration of a conventional oxygen sensor, as shown in FIG. 3(a), the cavity 31 formed in the insulator 4 is merely filled with the sealing material layer 32 which is mainly composed of glass. For example, when a bending stress is applied to the ceramic element 2 due to a shock caused by a flipped stone or thermal shock, stress concentration tends to occur in a boundary region between a portion of the ceramic element 2 covered with the sealing material layer 32 and an uncovered portion in the axial direction of the ceramic element 2, causing a potential breakage of the ceramic element 2.

By contrast, according to the above-described configuration of the oxygen sensor 1 of the present invention, as shown in FIG. 3(b), the cushion layers 33 and 34 made of a porous inorganic substance are disposed on opposite sides of the sealing material layer 32 with respect to the axial direction of the ceramic element 2. Accordingly, even when the force of a mechanical or thermal shock acts on the ceramic element 2, stress concentration is less likely to occur in the above-mentioned boundary region, so that breakage of the ceramic element 2 hardly occurs. In this case, since the cushion layers 33 and 34 support the portions of the ceramic element 2 which are not covered with the sealing material layer 32, stress can be dispersed which would otherwise concentrate at the sealing boundary portion.

When only a weak mechanical impact force acts on the sensor 1, the rear-end side cushion layer 33 may be omitted.

FIGS. 6(a) and 6(b) show the oxygen sensor 1 which is not equipped with the insulator 4. In FIGS. 6(a) and 6(b), the sealing material layer 32 and the cushion layer 34 are provided within the cavity 31 formed in the metallic shell 3 and are located between the surface of the cavity 31 and the outer surface of the ceramic element 2. An annular groove 43 that surrounds the sealing material layer 32 is formed in the metallic shell 3 by cutting out a portion of the metallic shell 3 and is located between the surface of the cavity 31 and the inner surface of the outer cylinder 18. A bottom 43a of the groove 43 is located beyond the sealing material layer 32 toward the tip of the ceramic element 2 with respect to the axial direction of the ceramic element 2.

Figure 7:
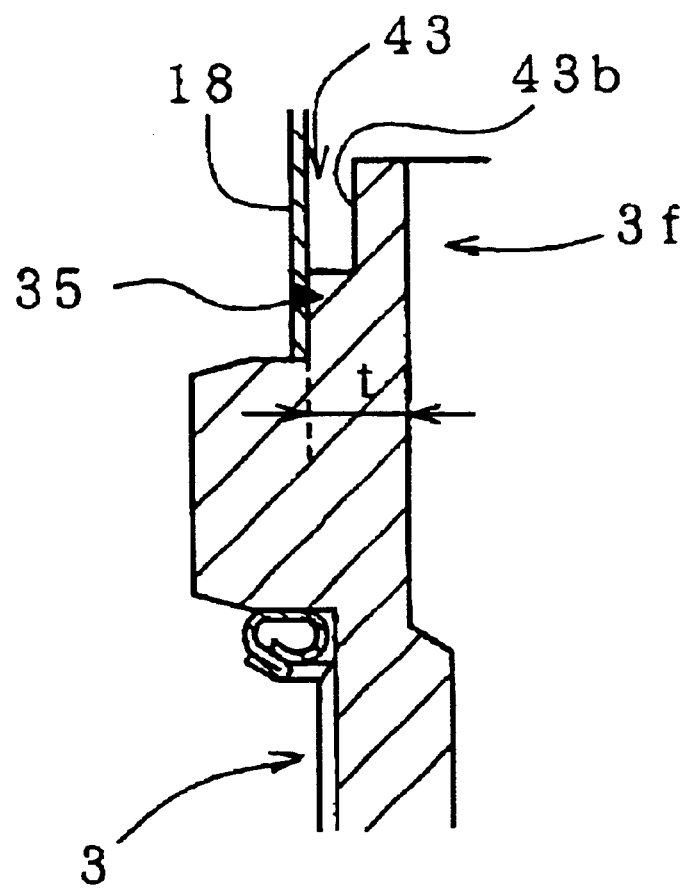
FIG. 7 is a longitudinal, sectional view showing a modification of the annular groove formed in the metallic shell.

The annular groove 43 may be formed in a manner as shown in FIG. 7. That is, the rear end portion of the metallic shell 3 is fitted into the outer cylinder 18. An annular cutout 43b is formed, and the groove 43 is defined by the outer cylinder 18 and the cutout 43b (in place of the cutout 43b, groove-shaped depressions may be formed at predetermined intervals in the circumferential direction). The metallic shell 3 and the outer cylinder 18 are connected through a welding portion 35 (or caulking portion) formed along the circumferential direction. This configuration is effective in the case where the thin-walled portion 3f of the metallic shell 3 in which the annular groove 43 is to be formed has a relatively small thickness t.

In the above embodiments, the gas sensor assumes the configuration of a λ sensor, which employs only an oxygen concentration cell element as a sensor element (ceramic element). However, the sensor element may be of a different type, such as a full-range oxygen sensor element or an $NO_x$ sensor element.

We claim:
1. A gas sensor comprising, in combination:
    a metallic shell having an end and defining a first longitudinal axial passageway;
    an outer cylinder secured to said end of said metallic shell;

a cylindrical insulator received in said first longitudinal axial passageway of said metallic shell and defining a second longitudinal axial passageway;

a sensor element received in said second axial longitudinal passageway of said cylindrical insulator for detecting a component of a measurement gas;

a cylindrical sealing material layer made of glass, located between said sensor element and said second axial longitudinal passageway of said cylindrical insulator and having a front surface and a rear surface spaced apart from each other along a longitudinal axis of said sealing material layer; and a first stress relieving cushion layer of a porous inorganic substance having a larger face and a smaller face spaced from said larger face along said longitudinal axis of said sealing material layer, said larger face disposed in contact with said front surface of said sealing material layer.

2. A gas sensor according to claim 1 wherein said first cushion layer is formed of a mixture containing filler particles which are superior in heat resistance to glass contained in said sealing material layer and clay binder particles which are superior in heat resistance to glass contained in said sealing material layer and are lower in softening temperature than the filler particles.

3. A gas sensor according to claim 2 wherein said filler particles are mainly $Al_2O_3$, and said binder particles are clay.

4. A gas sensor according to claim 1 wherein said first cushion layer has a rear face of a first diameter and a front face axially spaced from said rear face having a second diameter smaller than said first diameter.

5. A gas sensor according to claim 1 further including a second cushion layer disposed in contact with said rear surface of said sealing material layer such that said cushion layers are in contact with a respective one of said surfaces of said sealing material layer.

6. A gas sensor comprising, in combination:

a metallic shell joined to said outer cylinder and having an end and a through longitudinal passageway;

an outer cylinder secured to said end of said metallic shell;

an insulator disposed in said through longitudinal passageway and defining a second through longitudinal passageway;

a sensor element disposed inside said second through longitudinal passageway and for detecting a component of a measurement gas;

a cylindrical sealing material layer made of glass, disposed between said sensor element and said second through longitudinal passageway of said insulator and having a front surface and a rear surface spaced apart from each other along a longitudinal axis of said sealing material layer; and a first stress relieving cushion layer of a porous inorganic substance having a larger face and a smaller face axially spaced from said larger face along said longitudinal axis of said sealing material layer, said larger face disposed in contact with said front surface of said sealing material layer.

7. A gas sensor according to claim 6 wherein said first cushion layer is formed of a mixture containing filler particles which are superior in heat resistance to glass contained in said sealing material layer and clay binder particles which are superior in heat resistance to glass contained in said sealing material layer and are lower in softening temperature than the filler particles.

8. A gas sensor according to claim 7 wherein said filler particles are mainly $Al_2O_3$, and said binder particles are clay.

9. A gas sensor according to claim 6 further including a second cushion layer disposed in contact with said surface of said sealing material layer such that each of said cushion layers is in contact with a respective one of said surfaces of said sealing material layer.

* * * * *